United States Patent [19]

Iwasaki et al.

[11] Patent Number: 4,840,951
[45] Date of Patent: Jun. 20, 1989

[54] NOVEL NAPHTHALENE DERIVATIVE

[75] Inventors: Tameo Iwasaki, Nishinomiya; Kohki Takashima, Tokyo, both of Japan

[73] Assignee: Tanabe Seiyaku Co., Ltd., Osaku, Japan

[21] Appl. No.: 64,293

[22] Filed: Jun. 17, 1987

[30] Foreign Application Priority Data

Jul. 1, 1986 [JP] Japan ................................. 61-155416

[51] Int. Cl.$^4$ ................... C07C 265/30; A61K 31/235; A61K 31/535
[52] U.S. Cl. ................................. 514/239.5; 514/183; 514/222.2; 514/228.8; 514/277; 514/359; 514/408; 514/430; 514/438; 514/449; 514/463; 514/466; 514/468; 514/533; 514/534; 514/544; 514/510; 514/824; 544/2; 544/3; 544/59; 544/63; 544/106; 546/206; 546/400; 549/13; 549/14; 549/29; 549/30; 549/356; 549/359; 549/429; 560/51; 560/53; 560/56
[58] Field of Search ............................ 560/56, 53, 51; 514/510, 824, 239.5, 544, 183, 222.2, 228.8, 277, 359, 408, 430, 438, 449, 463, 466, 468, 533, 544; 544/106, 2, 3, 59, 6.3; 549/35.9, 13, 29, 356, 429, 14, 30; 546/206, 400

[56] References Cited

PUBLICATIONS

G. Traverso, "Intermedi necessari nella syntesi di taluni resinoli & loroderivati", *Gazzetta Chimica Italiana*, vol. 88, Fasc. VI–VII (1958).
Giorgio Traverso, "Intermediates for the Synthesis of Resinols and Derivatives", *Chem. Abstr.*, vol. 55, 20025i–20027i (1958).
Gonzalez et al., "Synthesis of Two Arylnaphthalene Lignans", *Tetrahedon*, vol. 34, 1011–1013 (1978).
Ghosal et al., "Two New Aryl Naphthalide Lignans from Polygala Chinensis", *Phytochemistry*, vol . 13, 1933–1936 (1974).
Plaumann et al., "Potential Isobenzofurans: Their Use in the Synthesis of Naturally Occurring 1-Arylnaphthalide Lignans", *J.C.S. Chem. Comm.*, 354–355 (1980).
de Silva et al., "A Regiocontrolled Synthesis of Some Arylnaphthalide Lignans", *J.C.S. Chem. Comm.*, 995–997, (1980).
Keay et al., "Hydroxyacetals, Phthalans, and Isobenzofurans Therefrom", *Can. J. Chem.*, vol. 61, 1987–1995 (1983).

*Primary Examiner*—Richard L. Raymond
*Assistant Examiner*—Raymond Covington
*Attorney, Agent, or Firm*—Browdy and Neimark

[57] ABSTRACT

Naphthalene derivative of the formula:

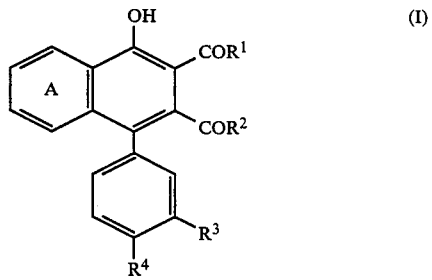

(I)

wherein Ring A is a substituted or unsubstituted benzene ring; each of $R^1$ and $R^2$ is a group of the formula: $-OR^5$, $-NHR^5$ or

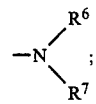

or either one of $R^1$ and $R^2$ is a lower alkoxy group and the other one is a group of the formula: $-OR^5$, $-NHR^5$ or

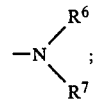

each of $R^3$ and $R^4$ is a lower alkoxy group, or one of $R^3$ and $R^4$ is a lower alkoxy group and the other is a hydrogen atom; $R^5$ is a substituted alkyl group, a heterocyclic group, a cycloalkyl group, an alkyl group of at least 5 carbon atoms or alkenyl group; and each of $R^6$ and $R^7$ is hydrogen atom or a lower alkyl group and salts thereof are disclosed. Said naphthalene derivative (I) and its salts have excellent hypolipidemic activity and are useful for treatment or prophylaxis of hyperlipidemia and/or arteriosclerosis.

24 Claims, No Drawings

NOVEL NAPHTHALENE DERIVATIVE

This invention relates to a novel naphthalene derivative and processes for preparing same. More particularly, it relates to a naphthalene derivative of the formula:

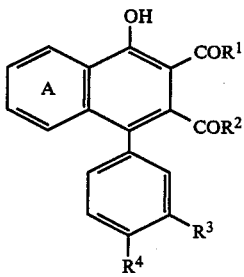

wherein Ring A is a substituted or unsubstituted benzene ring; each of $R^1$ and $R^2$ is a group of the formula: $-OR^5$, $-NHR^5$ or

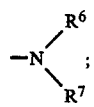

or either one of $R^1$ and $R^2$ is a lower alkoxy group and the other one is a group of the formula: $-OR^5$, $-NHR^5$ or

each of $R^3$ and $R^4$ is a lower alkoxy group, or one of $R^3$ and $R^4$ is a lower alkoxy group and the other is a hydrogen atom; $R^5$ is a substituted alkyl group, a heterocyclic group, a cycloalkyl group, an alkyl group of at least 5 carbon atoms or alkenyl group; and each of $R^6$ and $R^7$ is hydrogen atom or a lower alkyl group, and a salt thereof.

It is known that cholesterol in blood serum exists in various forms such as very-low density lipoprotein (VLDL) cholesterol, low density lipoprotein (LDL) cholesterol and high-density lipoprotein (HDL) cholesterol. It is also known that HDL has therapeutic or prophylactic effect for arteriosclerosis because of its preventing effect on deposition of cholesterol on arterial walls, while VLDL and LDL induce the deposition of cholesterol and are causative of arteriosclerosis [Annals of Internal Medicine, vol. 90, page 85-91 (1979)]. Therefore, in the field of therapy or prophylaxis of arteriosclerosis, it has been desired to develop a hypolipidemic agent which can decrease serum total cholesterol level and at the same time increase serum HDL-cholesterol level.

As a result of various investigations, we have now found that the naphthalene derivative (I) of the invention shows potent hypolipidemic activity and is useful for treatment or prophylaxis of hyperlipidemia which has been known to be one of the major causal factors of arteriosclerosis.

Thus, an object of the present invention is to provide a naphthalene derivative (I) which is useful for therapeutic treatment or prophylaxis of hyperlipidemia and/or arteriosclerosis. Another object is to provide a novel pharmaceutical composition for use as a hypolipidemic agent. The other object is to provide processes for preparing said naphthalene derivatives. Still other objects of the invention will be apparent from the following description and claims.

The naphthalene derivative (I) and the salt thereof have excellent hypolipidemic effect and are characterized in that they can decrease total cholesterol level and at the same time increase HDL-cholesterol level. For example, when the effect of a test compound on serum total cholesterol level and HDL-cholesterol level was examined by administrating it to rats fed up with the diet containing cholesterol (2 W/W %) and sodium cholate (0.5 W/W %), 1-(3,4-dimethoxyphenyl)-2-methoxycarbonyl-3-(pentan-3-yl-oxycarbonyl)-4-hydroxy-6,7,8-trimethoxynaphthalene of the present invention showed 66.8% decrease in serum total cholesterol level and 162.8% increase in HDL-cholesterol level at a dose of 100 mg/kg.

Moreover, the naphthalene derivative (I) is low in toxicity and substantially free from undesirable side effects such as hepatic dysfunction. For example, when the above-mentioned compound was administered orally to mice at a dose of 100 mg/kg, no mice died even 5 days after the administration and showed any decrease in body weight.

Representative examples of the naphthalene derivative of the invention include those of the formula (I) in which Ring A is (i) an unsubstituted benzene ring, (ii) a benzene ring having 1-3 substituent(s) selected from the group consisting of a lower alkyl group (e.g., methyl, ethyl, propyl or butyl group), a lower alkoxy group (e.g., methoxy, ethoxy, propoxy, isopropoxy or butoxy group), a phenyl-lower alkoxy group (e.g., benzyloxy or phenethyloxy group), hydroxy group and a halogen atom (e.g., fluorine, chlorine, bromine or iodine atom), or (iii) a benzene ring substituted with a lower alkylenedioxy group (e.g., methylenedioxy group or ethylenedioxy group);

each of $R^1$ and $R^2$ is a group of the formula: $-OR^5$, $-NHR^5$ or

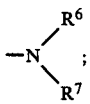

or either one of $R^1$ and $R^2$ is a lower alkoxy group (e.g., methoxy, ethoxy, propoxy or butoxy group), and the other one is a group of the formula: $-OR^5$, $-NHR^5$ or

each of $R^3$ and $R^4$ is a lower alkoxy group (e.g., methoxy, ethoxy, propoxy or butoxy group), or one of $R^3$ and $R^4$ is a lower alkoxy group (e.g., methoxy, ethoxy, propoxy or butoxy group) and the other is hydrogen atom; $R^5$ is either one of (i) an alkyl group having at least one substituent selected from a heterocyclic group containing nitrogen atom, oxygen atom and/or sulfur atom (e.g., pyridyl, morpholino, thiomorpholino, morpholinyl, thiomorpholinyl, imidazolyl, piperazinyl, furyl, tetrahydropyranyl, thienyl, thiazolyl or oxazolyl group), an aryl group (e.g., phenyl, nitrophenyl, methoxyphenyl, halogenophenyl, tolyl, xylyl or naphthyl group), a cycloalkyl group (e.g., cyclopentyl, cyclohexyl, cycloheptyl or cyclooctyl group), an alkylthio group (e.g., methylthio, ethylthio, propylthio or butylthio group), a lower alkoxy group (e.g., methoxy, ethoxy, propoxy or butoxy group), a lower alkoxycarbonyl group (e.g., methoxycarbonyl, ethoxycarbonyl, propoxycarbonyl or butoxycarbonyl group), a lower alkoxy-lower alkoxy group (e.g., methoxymethoxy, methoxybutoxy, butoxymethoxy or butoxybutoxy group), a mono-or di-lower alkylamino group (e.g., methylamino, ethylamino, propylamino, butylamino, dimethylamino, diethylamino, dipropylamino or dibutylamino group), amino group, thiol group, hydroxy group, carboxy group and a halogen atom (e.g., fluorine, chlorine, bromine or iodine atom), (ii) a heterocyclic group containing nitrogen atom, oxygen atom and/or sulfur atom (e.g., pyridyl, morpholino, thiomorpholino, morpholinyl, thiomorpholinyl, imidazolyl, piperazinyl, furyl, tetrahydropyranyl, thienyl, thiazolyl or oxazolyl group), (iii) a cycloalkyl group (e.g., cyclopentyl, cyclohexyl, cycloheptyl or cyclooctyl group), (iv) an alkyl group of at least 5 carbon atoms (e.g., pentyl, hexyl, heptyl, octyl, nonyl or decyl group), or (v) an alkenyl group (e.g., vinyl, allyl, butenyl, butadienyl or decadienyl group); each of $R^6$ and $R^7$ is hydrogen atom or a lower alkyl group (e.g., methyl, ethyl, propyl or butyl group).

Among the compounds mentioned above, preferred examples of the naphthalene derivative include those of the formula (I) in which Ring A is an unsubstituted benzene ring, a benzene ring having 1–3 substituent(s) selected from an alkoxy group of 1–4 carbon atoms and a halogen atom or a benzene ring substituted with an alkylenedioxy group of 1 or 2 carbon atoms; each of $R^1$ and $R^2$ is a group of the formula: $-OR^5$, $-NHR^5$ or

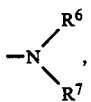

or either one of $R^1$ and $R^2$ is a lower alkoxy group of 1–4 carbon atoms and the other one is a group of the formula: $-OR^5$, $-NHR^5$ or

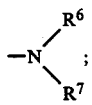

each of $R^3$ and $R^4$ is an alkoxy group of 1–4 carbon atoms, or one of $R^3$ and $R^4$ is an alkoxy group of 1–4 carbon atoms and the other is hydrogen atom; $R^5$ is either one of (i) an alkyl group of 1–4 carbon atoms having 1 or 2 substituent(s) selected from a 5- or 6-membered nitrogen-containing monocyclic heterocyclic group, phenyl group, a cycloalkyl group of 5–8 carbon atoms, an alkoxy group of 1 or 2 carbon atoms, an alkylthio group of 1 or 2 carbon atoms, an alkoxy-alkoxy group of 2–4 carbon atoms, a dialkylamino group of 2–4 carbon atoms, hydroxy group and a halogen atom, (ii) a 5- or 6-membered nitrogen-containing monocyclic heterocyclic group, (iii) a cycloalkyl group of 5–8 carbon atoms, (iv) an alkyl group of 5–10 carbon atoms or (v) an alkenyl group of 2–10 carbon atoms; and each of $R^6$ and $R^7$ is hydrogen atom or an alkyl group of 1–4 carbon atoms.

Another preferred examples of the naphthalene derivative include those of the formula (I) in which Ring A is an unsubstituted benzene ring, a benzene ring having 1–3 substituent(s) selected from an alkoxy group of 1–4 carbon atoms and a halogen atom or a benzene ring substituted with an alkylenedioxy group of 1 or 2 carbon atoms; each of $R^1$ and $R^2$ is a group of the formula: $-OR^5$, or one of $R^1$ and $R^2$ is a group of the formula: $-OR^5$ and the other is an alkoxy group of 1–4 carbon atoms; each of $R^3$ and $R^4$ is an alkoxy group of 1–4 carbon atoms; and $R^5$ is either one of (i) an alkyl group of 1–4 carbon atoms having 1 or 2 substituent(s) selected from a 5- or 6-membered nitrogen-containing monocyclic heterocyclic group, phenyl group, a cycloalkyl group of 5–8 carbon atoms, an alkoxy group of 1 or 2 carbon atoms, an alkylthio group of 1 or 2 carbon atoms, an alkoxy-alkoxy group of 2–4 carbon atoms, a dialkylamino group of 2–4 carbon atoms, hydroxy group and chlorine atom, (ii) a 5- or 6-membered nitrogen-containing monocyclic heterocyclic group, (iii) a cycloalkyl group of 5–8 carbon atoms, (iv) an alkyl group of 5–10 carbon atoms or (v) an alkenyl group of 2–10 carbon atoms.

Still another preferred examples of the naphthalene derivative include those of the formula (I) in which Ring A is a benzene ring having three substituents selected from an alkoxy group of 1–4 carbon atoms or a benzene ring substituted with an alkylenedioxy group of 1 or 2 carbon atoms; one of $R^1$ and $R^2$ is a group of the formula: $-OR^5$, and the other is an alkoxy group of 1–4 carbon atoms; each of $R^3$ and $R^4$ is an alkoxy group of 1–4 carbon atoms; and $R^5$ is either one of (i) an alkyl group of 1–4 carbon atoms having 1 or 2 substituent(s) selected from a 5- or 6-membered nitrogen-containing monocyclic heterocyclic group, phenyl group, a cycloalkyl group of 5–8 carbon atoms, an alkoxy group of 1 or 2 carbon atoms, an alkylthio group of 1 or 2 carbon atoms, an alkoxy-alkoxy group of 2–4 carbon atoms, a dialkylamino group of 2–4 carbon atoms, hydroxy group and chlorine atom, (ii) a 5- or 6-membered nitrogen-containing monocyclic heterocyclic group, (iii) a cycloalkyl group of 5–8 carbon atoms, (iv) an alkyl group of 5–10 carbon atoms or (v) an alkenyl group of 2–10 carbon atoms.

Other preferred examples of the naphthalene derivative include those of the formula (I) in which Ring A is an unsubstituted benzene ring or a benzene ring having 1–3 substituent(s) selected from an alkoxy group of 1–4 carbon atoms and a halogen atom; each of $R^1$ and $R^2$ is (i) an alkoxy group of 1–4 carbon atoms having a substituent selected from phenyl group, a cycloalkyl group of 5–8 carbon atoms and an alkoxy-alkoxy group of 2–4 carbon atoms, (ii) a cycloalkyloxy group of 5–8 carbon atoms or (iii) an alkoxy group of 5-10 carbon atoms; and each of $R^3$ and $R^4$ is an alkoxy group of 1-4 carbon atoms.

Still other preferred examples of the naphthalene derivative include those of the formula (I) in which Ring A is a benzene ring having three substituents selected from an alkoxy group of 1-4 carbon atoms; either one of $R^1$ and $R^2$ is a phenylalkylamino group of 7 or 8 carbon atoms, a monoalkylamino group of 1-4 carbon atoms or a dialkylamino group of 2-8 carbon atoms, and the other one is an alkoxy group of 1-4 carbon atoms; and each of $R^3$ and $R^4$ is an alkoxy group of 1-4 carbon atoms.

Examples of the salts of the naphthalene derivative (I) include alkali metal salts (e.g., sodium salts, potassium salt), alkaline earth metal salts (e.g., calcium salt, etc.), quarternary ammonium salts (e.g., tetramethylammonium salt, tetraethylammonium salt) and so forth. Moreover, when at least either one of $R^1$ and $R^2$ is a nitrogen-containing group, the naphthalene derivative (I) of the present invention may form acid addition salts. Examples of such acid addition salts include inorganic acid addition salts (e.g., hydrochloride, hydrobromide, sulfate), organic acid addition salts (e.g., formate, acetate, p-toluenesulfonate, methanesulfonate) and so forth.

The daily dose of the naphthalene derivative (I) is preferably in the range of 1.5-35 mg/kg, especially 5-25 mg/kg, though it may vary depending on the type and severity of diseases; and/or ages, weight and conditions of patients.

Further, the naphthalene derivative (I) may be administered either orally or parenterally, while it is preferred to administer it through oral route. When administered orally, it may be used in solid form such as tablets, powders, capsules and granules. Such pharmaceutical preparations may contain conventional excipients, binding agents, diluents, disintegrants, wetting agents and the like. Alternatively, it may be administered orally in liquid form such as aqueous or oily suspensions, solutions, syrups, elixirs and the like. On the other hand, when administered parenterally, it may be used in the form of injections and suppositories.

The naphthalene derivative (I) and the pharmaceutically acceptable salt thereof have excellent hypolipidemic effect and may be used for the therapeutic treatment or prophylaxis of hyperlipidemia (e.g., hypercholesterolemia), arteriosclerosis (e.g., atherosclerosis, Mönckeberg sclerosis) and the like.

According to the present invention, the naphthalene derivative (I) may be prepared by condensing an acetylene compound of the formula:

wherein $R^1$ and $R^2$ are the same as defined above, or a salt thereof with an aldehyde compound of the formula:

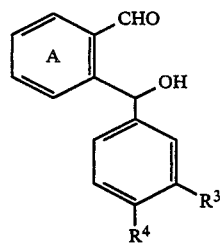

wherein Ring A, $R^3$ and $R^4$ are the same as defined above, a di-lower alkyl acetal thereof or a salt thereof.

Alternatively, the naphthalene derivative (I) may be prepared by reacting a 3-naphthoic acid compound of the formula:

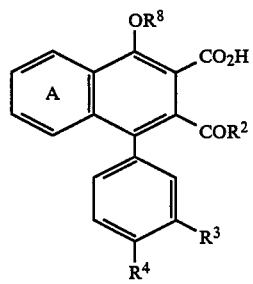

wherein $OR^8$ is hydroxy group or a protected hydroxy group, and Ring A, $R^2$, $R^3$ and $R^4$ are the same as defined above, or a salt thereof with a compound of the formula:

wherein $R^1$ is the same as defined above, or a salt thereof and, if required, removing the protecting group therefrom.

In carrying out the above-mentioned reactions, the starting compounds (II)–(V) may be, if required, used in the form of a salt thereof. For example, the starting compounds (II), (IV) and (V) in which at least either one of $R^1$ and $R^2$ is a group containing at least one nitrogen atom may be used in the form of inorganic acid addition salts such as hydrochloride, hydrobromide and sulfate, or organic acid addition salts such as formate, acetate, p-toluenesulfonate and methanesulfonate. On the other hand, the aldehyde compound (III) or its di-lower alkyl acetal and the 3-naphthoic acid compound (IV) may be used for the reactions in the form of either alkali metal salts (e.g., sodium salt, potassium salt), alkaline earth metal salts (e.g., calcium salt) or quarternary ammonium salts (e.g., tetramethylammonium salt, tetraethylammonium salt). The starting compounds (II) and (V) in which at least either one of $R^1$ and $R^2$ is a group containing thiol group, hydroxy group and/or carboxy group may also be used in the form of alkali metal, alkaline earth metal or quarternary ammonium salts as mentioned above.

Examples of the protecting group ($R^8$) for the hydroxy group at 4-position of the 3-naphthoic acid compound (IV) include a substituted or unsubstituted phenyl-lower alkyl group (e.g., benzyl group, p-methoxybenzyl group, 3,4-dimethoxybenzyl group), a lower alkoxy-alkyl group (e.g., methoxymethyl group, ethoxymethyl group, methoxyethoxymethyl group) and the like.

The condensation of the acetylene compound (II) or a salt thereof with the aldehyde compound (III), its di-lower alkyl acetal or a salt thereof may be conducted in the presence of an acid in or without a solvent. Examples of the di-lower alkyl acetal of the aldehyde compound (III) include dimethylacetal, diethylacetal, dipropylacetal, dibutylacetal and the like. Suitable examples of said acid include inorganic acid such as hydrochloric acid and sulfuric acid, and organic acid such as formic acid, acetic acid, trifluoroacetic acid, p-toluenesulfonic acid and methanesulfonic acid. Benzene, toluene, xylene, dimethylformamide and the like are suitable as the solvent. It is preferred to carry out the reaction at a temperature between $-70°$ C. and $150°$ C., especially between $50°$ C. and $100°$ C.

On the other hand, the reaction of the 3-naphthoic acid compound (IV) or a salt thereof with the compound (V) or a salt thereof may be conducted in the presence of dehydrating agent in a solvent. Conventional dehydrating agent such as a mixture of diazenedicarboxylic acid diester compound (e.g., diazenedicarboxylic acid diethyl ester, diazenedicarboxylic acid dibenzyl ester) and triphenylphosphine, N,N'-dicyclohexylcarbodiimide, a mixture of N,N'-dicyclohexylcarbodiimide and 1-hydroxybenzotriazol may be used for this reaction. Tetrahydrofuran, dioxane, dimethylformamide, benzene, ethyl acetate and the like are suitable as the solvent. It is preferred to carry out the reaction at a temperature between $-70°$ C. and $50°$ C., especially between $-15°$ C. and room temperature. When $R^1$ is a group of the formula: $-OR^5$ or $-NHR^5$ and $R^5$ is a mono- or di-hydroxyalkyl group, said hydroxy group or groups may be protected during the above-mentioned reaction of the starting compounds (IV) and (V). Suitable examples of the protecting group or groups to be used for this purpose include a substituted or unsubstituted phenyl-lower alkyl group (e.g., benzyl group, p-methoxybenzyl group, 3,4-dimethoxybenzyl group), a lower alkoxymethyl group (e.g., methoxymethyl group, ethoxymethyl group) and a lower alkylidene group (e.g., methylidene group, ethylidene group, propylidene group, isopropylidene group, butylidene group).

The subsequent removal of the protecting group or groups from the above-mentioned reaction product may be conducted according to a conventional manner such as catalytic hydrogenation, hydrolysis and the like. For example, when the protecting group is the substituted or unsubstituted phenyl-lower alkyl group, it may be removed by catalytic hydrogenation in the presence of a catalyst such as palladium charcoal and platinum. On the other hand, when the protecting group is a lower alkoxymethyl group or a lower alkylidene group, it may be removed by hydrolysis with an acid or alkali agent.

The naphthalene derivative (I) in free form may be readily converted into the salts thereof by a conventional manner, for example, treating the former compound with an alkali metal or alkaline earth metal hydroxide, a quarternary ammonium hydroxide, an inorganic acid, an organic acid and the like.

Concomitantly, among the starting compounds of the present invention, the aldehyde compound (III) and its di-lower alkyl acetal may be prepared by reacting a benzaldehyde compound of the formula:

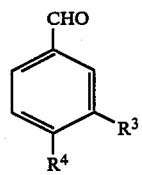

wherein $R^3$ and $R^4$ are the same as defined above, with a di-alkylacetal compound of the formula:

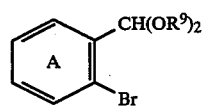

wherein $R^9$ is a lower alkyl group and Ring A is the same as defined above, in the presence of an alkyl lithium (e.g., n-butyl lithium, sec-butyl lithium, tert-butyl lithium) in a solvent at a temperature between $-80°$ C. and $0°$ C., and if required, further treating the product with an acid.

On the other hand, the starting compound (IV) may be prepared by reacting an aldehyde compound (III) or a di-lower alkyl acetal thereof with an acetylene derivative of the formula:

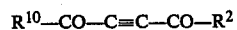

wherein $R^{10}$ is a lower alkoxy group, and $R^2$ is the same as defined above, under the same condition as mentioned in the reaction of the compounds (II) and (III), optionally introducing a protecting group on the hydroxy group at 4-position of the product, and then hydrolysing the ester moiety ($R^{10}$) at 3-position thereof according to a conventional manner.

EXPERIMENT (Effect on serum total cholesterol level and serum HDL-cholesterol level)

METHOD

Male SD rats (body weight: 140 to 200 g, one group consisting of 5 rats) were fed ad libitum for 4 days with a diet containing 2 W/W % of cholesterol and 0.5 W/W % of sodium cholate. Then, the rats were further fed ad libitum with the same diet containing 100 mg % of a test compound. The control group of rats were fed with the diet not containing the test compound. Three days later, the rats were anesthetized with ether. After the body weights of the rats were measured, blood was collected from abdominal aorta thereof. The blood was allowed to stand at room temperature for one hour and centrifuged. Then, the total cholesterol level in the serum thus obtained was measured enzymatically according to the method described in Clinical Chemistry, vol. 20, page 470 (1974). On the other hand, HDL-cholesterol in the above-obtained serum was obtained as soluble fractions after precipitating VLDL- and LDL-cholesterol using dextran sulfate [Canadian Journal of Biochemistry, vol. 47, page 1043 (1969)], and then serum HDL-cholesterol level was measured enzymatically according to the above-mentioned method. On the basis of the results obtained above, the effects of the test compound on the serum total cholesterol level and serum HDL-cholesterol level were calculated according to the formulae:

PERCENTAGE DECREASE IN
SERUM TOTAL CHOLESTEROL LEVEL =

$$\left[1 - \frac{\text{Average value of serum total cholesterol level in the medicated group of rats}}{\text{Average value of serum total cholesterol level in the control group of rats}}\right] \times 100$$

PERCENTAGE INCREASE IN
SERUM HDL-CHOLESTEROL LEVEL =

$$\left[\frac{\text{Average value of serum HDL-cholesterol level in the medicated group of rats}}{\text{Average value of serum HDL-cholesterol level in the control group of rats}} - 1\right] \times 100$$

RESULTS

The results are shown in the following Table 1.

TABLE 1

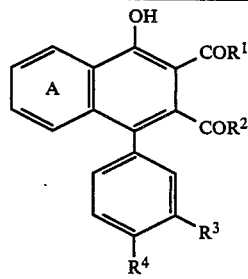
(I)

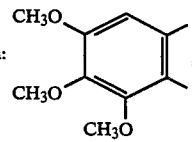

[Ring A is a benzene ring of the formula: (shown above), and both of $R^3$ and $R^4$ are methoxy group.]

| Test Compound (I) | | Percentage Decrease in serum total cholesterol level | Percentage Increase in serum HDL-cholesterol level |
|---|---|---|---|
| $R^1$ | $R^2$ | | |
| OCH(C$_2$H$_5$)$_2$ | —OCH$_3$ | 66.8 | 162.8 |
| —OCH$_2$CH$_2$OCH$_3$ | —OCH$_3$ | 66.1 | 111.1 |
| —O(CH$_2$)$_2$SC$_2$H$_5$ | —OCH$_3$ | 64.6 | 163.0 |
| —N(C$_2$H$_5$)$_2$ | —OCH$_3$ | 64.5 | 87.8 |
| —OCH$_2$-(2-pyridyl)·HCl | —OHC$_3$ | 63.7 | 192.3 |
| —OCH$_2$[CH(OH)]$_2$H | —OCH$_3$ | 60.7 | 169.8 |
| —NHCH$_2$CH(CH$_3$)$_2$ | —OCH$_3$ | 60.0 | 99.0 |
| —O-(2-pyridyl)·HCl | —OCH$_3$ | 57.3 | 103.2 |
| —(OCH$_2$CH$_2$)$_3$H | —OCH$_3$ | 53.9 | 123.0 |
| —OCH$_2$CH$_2$N(C$_2$H$_5$)$_2$·HCl | —OCH$_3$ | 52.0 | 70.7 |
| —OCH$_2$-phenyl | —OCH$_3$ | 50.8 | 141.5 |
| —OCH$_2$CH$_2$—N(morpholino)·HCl | —OCH$_3$ | 49.4 | 111.0 |

TABLE 1-continued

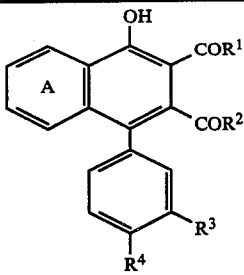

| Ring A is a benzene ring of the formula: 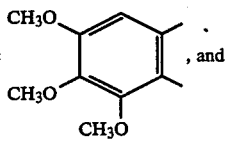 , and both of $R^3$ and $R^4$ are methoxy group. |

| Test Compound (I) | | Percentage Decrease in serum total cholesterol level | Percentage Increase in serum HDL-cholesterol level |
| --- | --- | --- | --- |
| $R^1$ | $R^2$ | | |
| —OCH₂—⟨cyclohexyl-H⟩ | —OCH₃ | 48.2 | 140.1 |
| —OCH₂CH=CH₂ | —OCH₃ | 48.1 | 120.7 |
| —OCH₂—⟨phenyl⟩ | —OCH₂—⟨phenyl⟩ | 46.5 | 109.4 |
| —OCH₂—⟨cyclohexyl-H⟩ | —OCH₂—⟨cyclohexyl-H⟩ | 44.2 | 121.5 |
| —O—⟨cyclohexyl-H⟩ | —OCH₃ | 42.9 | 135.5 |

Immediately after the collection of blood in the above-mentioned experiments, the liver of each rat was taken out, and the weight thereof was measured. Then, the relative liver weight was calculated according to the following formula, and the average relative liver weight was compared with that of the control group. The test compounds used in the above-mentioned experiments showed no substantial increase in the relative liver weight.

$$\text{RELATIVE LIVER WEIGHT} = \frac{\text{Liver weight}}{\text{Body weight}} \times 100$$

EXAMPLE 1

A mixture of 6 g of 2-(α-hydroxy-3,4-dimethoxybenzyl)-3,4,5-trimethoxybenzaldehyde dimethylacetal, 3.8 g of dihexyl acetylenedicarboxylate and 6 ml of acetic acid is refluxed for 2 hours. The reaction mixture is concentrated under reduced pressure. The residue is subjected to silica gel column chromatography [solvent: hexane-ethyl acetate (2:1)], and the eluate is evaporated to remove the solvent. The thus-obtained residue is recrystallized from methanol, whereby 5.2 g of 1-(3,4-dimethoxyphenyl)-2,3-bis(hexyloxycarbonyl)-4-hydroxy-6,7,8-thrimethoxynaphthalene are obtained as colorless needles.

M.p. 67° C.

NMR (CDCl₃) δ: 0.7–1.9 (m, 22H), 3.20 (s, 3H), 3.75 (t, 2H), 3.76 (s, 3H), 3.82 (s, 3H), 3.85 (s, 3H), 3.95 (s, 3H), 4.27 (t, 2H), 6.70 (s, 3H), 7.53 (s, 1H), 12.37 (s, 1H)

IR $\nu_{Max}^{Nujol}$ (cm⁻¹): 1720, 1660, 1590, 1520

EXAMPLES 2–6

The corresponding starting compounds are treated in the same manner as described in Example 1, whereby the compounds listed in Table 2 are obtained.

TABLE 2

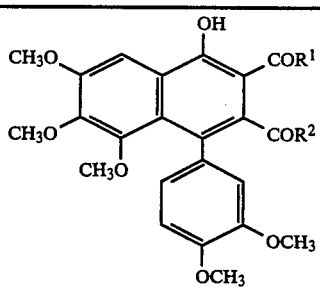

| Example Nos. | Compound (I-a) R¹ and R² | Physical properties |
|---|---|---|
| 2 | —OCH(C₂H₅)₂ | oil, NMR (CDCl₃)δ: 0.5–2.0 (m, 20H), 3.14 (s, 3H), 3.74 (s, 3H), 3.78 (s, 3H), 3.81 (s, 3H), 3.93 (s, 3H), 4.2–4.6 (m, 1H), 4.9–5.2 (m ,1H), 6.70 (s, 3H), 7.52 (s, 1H), 12.40 (s, 1H) |
| 3 | —O—⌬H (cyclopentyl) | m.p. 148° C. IR$\nu_{Max}^{Nujol}$ (cm$^{-1}$): 1710, 1650, 1590, 1520 |
| 4 | —OCH₂—⌬H (cyclohexyl) | m.p. 116° C. IR$\nu_{Max}^{Nujol}$ (cm$^{-1}$): 1720, 1640, 1590, 1510 |
| 5 | —OCH₂—⌬ (phenyl) | m.p. 130–132° C. IR$\nu_{Max}^{Nujol}$ (cm$^{-1}$): 1725, 1655, 1590, 1510 |
| 6 | —(OCH₂CH₂)₃H | m.p. 60–62° C. IR$\nu_{Max}^{Nujol}$ (cm$^{-1}$): 1745, 1655, 1585, 1500 |

EXAMPLE 7

(1) 2.6 g of 1-(3,4-dimethoxyphenyl)-2-methoxycarbonyl-4-methoxymethoxy-6,7,8-trimethoxy-3-naphthoic acid, 0.56 g of n-hexyl alcohol and 1.37 g of triphenylphosphine are dissolved in 20 ml of tetrahydrofuran. A solution of 0.96 g of diazenedicarboxylic acid diethyl ester in 5 ml of tetrahydrofuran is added dropwise thereto under stirring and ice-cooling for 5 minutes. The mixture is stirred for 3 hours at room temperature, and then evaporated to remove the solvent. The residue is purified by silica gel column chromatography [solvent: ethyl acetate-hexane (2:1)], whereby 2.5 g of 1-(3,4-dimethoxyphenyl)-2-methoxycarbonyl-3-n-hexyloxycarbonyl-4-methoxymethoxy-6,7,8-trimethoxynaphthalene are obtained as pale yellow oil.

NMR (CDCl₃) δ: 0.7–2.0 (m, 11H), 3.25 (s, 3H), 3.45 (s, 3H), 3.67 (s, 3H), 3.82 (s, 3H), 3.86 (s, 3H), 3.90 (s, 3H), 4.00 (s, 3H), 4.29 (t, 2H), 5.21 (s, 2H), 6.81 (s, 3H), 7.85 (s, 1H)

(2) 20 ml of trifluoroacetic acid and 2 ml of water are added to 2.5 g of the above-obtained product, and the mixture is stirred at room temperature for 30 minutes. The reaction mixture is evaporated under reduced pressure to remove the solvent, and the residue is dissolved in 100 ml of ethyl acetate. The solution is washed with water, dried and evaporated to remove the solvent under reduced pressure. The residue is purified by silica gel column chromatography [solvent: chloroform], and the eluate is evaporated to remove the solvent. The residue is recrystallized from isopropylether, whereby 1.6 g of 1-(3,4-dimethoxyphenyl)-2-methoxycarbonyl-3-n-hexyloxycarbonyl-4-hydroxy-6,7,8-trimethoxynaphthalene are obtained as colorless needles.

M.p. 119°–120° C.

NMR (CDCl₃) δ: 0.6–1.9 (m, 11H), 3.20 (s, 3H), 3.36 (s, 3H), 3.77 (s, 3H), 3.81 (s, 3H), 3.84 (s, 3H), 3.95 (s, 3H), 4.25 (t, 2H), 6.70 (s, 3H), 7.52 (s, 1H), 12.34 (s, 1H)

IR $\nu_{Max}^{Nujol}$ (cm$^{-1}$): 1735, 1650, 1605, 1585, 1510

EXAMPLES 8–24

The corresponding starting compounds are treated in the same manner as described in Example 7, whereby the compounds listed in Table 3 are obtained. [Example 19 is carried out by using 2,3-isopropylidenedioxypropanol as the starting compound (V) instead of n-hexyl alcohol, followed by treatment of the product with trifluoroacetic acid to remove the protecting groups (i.e., isopropylidene group used to protect the adjacent hydroxy groups and the protecting group of hydroxy group at 4-position of naphthalene derivative (I)) therefrom.]

TABLE 3

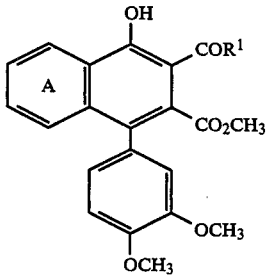

In Examples 8–23, Ring A is a group of the formula:

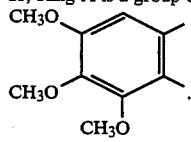

On the other hand, in Example 24, Ring A is a group of the formula:

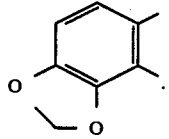

| Example Nos. | Compound (I-b) R¹ | Physical properties |
|---|---|---|
| 8 | —OCH(C₂H₅)₂ | m.p. 130–132° C. IR$\nu_{Max}^{Nujol}$ (cm$^{-1}$); 1740, 1650, 1590, 1510 |
| 9 | —O—⌬H | m.p. 157–158° C. IR$\nu_{Max}^{Nujol}$ (cm$^{-1}$): 1735, 1645, 1590, 1510 |
| 10 | —OCH₂—⌬H | m.p. 126–127° C. IR$\nu_{Max}^{Nujol}$ (cm$^{-1}$): 1730, 1645, 1590, 1520 |

TABLE 3-continued

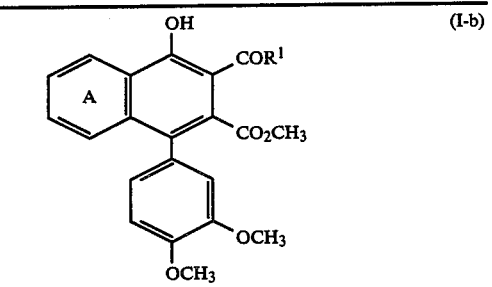

(I-b)

[In Examples 8-23, Ring A is a group of the formula:

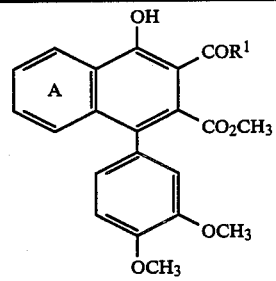

On the other hand, in Example 24, Ring A is a group of the formula:

]

| Example Nos. | Compound (I-b) $R^1$ | Physical properties |
|---|---|---|
| 11 | —O—n-$C_{10}H_{21}$ | m.p. 93° C.<br>IR$\nu_{Max}^{Nujol}$ (cm$^{-1}$):<br>1740, 1650, 1590, 1520 |
| 12 | —O$CH_2CH$=$CH_2$ | m.p. 156-157° C.<br>IR$\nu_{Max}^{Nujol}$ (cm$^{-1}$):<br>1740, 1660, 1605, 1590, 1510 |
| 13 | —O[$CH_2CH$=$C(CH_3)CH_2$]$_2$H | oil<br>IR$\nu_{Max}^{Nujol}$ (cm$^{-1}$):<br>1735, 1655, 1590, 1520 |
| 14 | —O—$CH_2$—phenyl | m.p. 174-175° C.<br>IR$\nu_{Max}^{Nujol}$ (cm$^{-1}$):<br>1740, 1660, 1610, 1590, 1510 |
| 15 | —O—pyridyl·HCl | m.p. 140-141° C.<br>IR$\nu_{Max}^{Nujol}$ (cm$^{-1}$):<br>2120, 2040, 1950, 1740, 1690, 1600, 1590 |
| 16 | —O—$(CH_2)_2OCH_3$ | m.p. 147-148° C.<br>IR$\nu_{Max}^{Nujol}$ (cm$^{-1}$):<br>1740, 1660, 1600, 1590, 1510 |
| 17 | —(O$CH_2CH_2$)$_3$H | m.p. 121-122° C.<br>IR$\nu_{Max}^{Nujol}$ (cm$^{-1}$):<br>1725, 1660, 1585, 1510 |
| 18 | —O$(CH_2)_2SC_2H_5$ | m.p. 132-135° C.<br>IR$\nu_{Max}^{Nujol}$ (cm$^{-1}$):<br>1730, 1650, 1590, 1520 |
| 19 | —O—$CH_2$[CH(OH)]$_2$H | m.p. 166-167° C.<br>IR$\nu_{Max}^{Nujol}$ (cm$^{-1}$):<br>3520, 3460, 1690, 1665, 1590, 1515 |
| 20 | —O—$(CH_2)_2N(C_2H_5)_2$·HCl | m.p. 199° C. (decomp.)<br>IR$\nu_{Max}^{Nujol}$ (cm$^{-1}$):<br>2300, 1720, 1680, 1590, 1515 |
| 21 | —O—$(CH_2)_2N$-morpholino·HCl | m.p. 209° C. (decomp.)<br>IR$\nu_{Max}^{Nujol}$ (cm$^{-1}$):<br>2130, 1730, 1660, 1590, 1520 |
| 22 | —O—$CH_2CHClCH_3$ | mp.p 143-144° C.<br>IR$\nu_{Max}^{Nujol}$ (cm$^{-1}$):<br>1740, 1660, 1600, 1585, 1510 |
| 23 | —O—$CH_2$-(2-pyridyl)·HCl | m.p. 122-123° C.<br>IR$\nu_{Max}^{Nujol}$ (cm$^{-1}$):<br>1720, 1660, 1590 |
| 24 | —O—$CH_2CHClCH_3$ | m.p. 187-189° C.<br>IR$\nu_{Max}^{Nujol}$ (cm$^{-1}$):<br>1740, 1630, 1580, 1520 |

EXAMPLE 25

1.4 g of 1-(3,4-dimethoxyphenyl)-2-methoxycarbonyl-4-benzyloxy-6,7,8-trimethoxy-3-naphthoic acid, 183 mg of isobutylamine and 336 mg of 1-hydroxybenzotriazol are dissolved in 15 ml of tetrahydrofuran. 570 mg of N,N'-dicyclohexylcarbodiimide are added thereto under stirring and ice-cooling, and the mixture is stirred for 2 hours at the same temperature and for 12 hours at room temperature. The reaction mixture is evaporated to remove the solvent. 50 ml of acetone is added to the residue, and insoluble materials are removed by filtration. The filtrate is evaporated to remove the solvent, and the residue is purified by silica gel column chromatography [solvent: chloroform-acetone (20:1)]. The eluate is evaporated to remove the solvent. The residue (pale yellow oil) is dissolved in 30 ml of methanol, and 200 mg of palladium-charcoal are added thereto. The mixture is stirred for 2 hours in hydrogen gas atmosphere under 3 kg/cm² pressure. The catalyst is removed from the reaction mixture by filtration, and the residue is recrystallized from a mixture of ethyl acetate and petroleum ether, whereby 1.1 g of 1-(3,4-dimethoxyphenyl)-2-methoxycarbonyl-3-isobutylcarbamoyl-4-hydroxy-6,7,8-trimethoxynaphthalene are obtained as colorless crystals.

M.p. 135°–137° C.

NMR (CDCl$_3$) δ: 0.93 (d, 6H), 1.5–2.0 (m, 1H), 3.15 (t, 2H), 3.20 (s, 3H), 3.35 (s, 3H), 3.73 (s, 3H), 3.76 (s, 3H), 3.81 (s, 3H), 3.92 (s, 3H), 6.67 (s, 3H), 6.6–7.0 (br, 1H), 7.47 (s, 1H), 13.06 (s, 1H)

IR $\nu_{Max}^{Nujol}$ (cm$^{-1}$): 3400, 1740, 1620, 1580

EXAMPLES 26 and 27

The corresponding starting compounds are treated in the same manner as described in Example 25, whereby the compounds listed in Table 4 are obtained.

TABLE 4

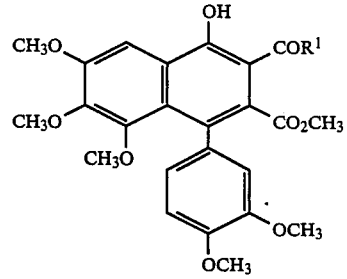

(I-c)

| Example Nos. | Compound (I-c) R$^1$ | Physical properties |
|---|---|---|
| 26 | —N(CH$_2$CH$_3$)$_2$ | m.p. 162–163° C. IR$\nu_{Max}^{Nujol}$ (cm$^{-1}$): 1745, 1720, 1600 |
| 27 | —NHCH$_2$CH$_2$—C$_6$H$_5$ | m.p. 142–143° C. IR$\nu_{Max}^{Nujol}$ (cm$^{-1}$): 3400, 1740, 1620, 1590 |

EXAMPLES 28–31

The corresponding starting compounds are treated in the same manner as described in Example 1, whereby the compounds listed in Table 5 are obtained.

TABLE 5

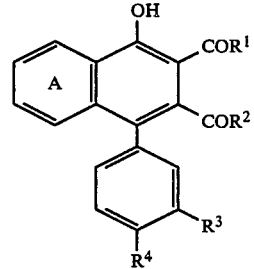

(I-d)

| Example Nos. | Ring A | R$^1$ and R$^2$ | Physical Properties |
|---|---|---|---|
| 28 | (benzene ring) | —(OCH$_2$CH$_2$)$_3$—H | oil, NMR(CDCl$_3$) δ: 1.15(t, 6H), 3.3–4.0(m, 16H), 4.10 (t, 2H), 4.45(t, 2H), 6.7–7.0(m, 3H), 7.3–7.6(m, 3H), 8.2–8.5(m, 1H), 12.11(s, 1H) |
| 29 | (3,4-dichlorophenyl ring) | —O—n-C$_6$H$_{13}$ | m.p. 123–125° C. IR$\nu_{Max}^{Nujol}$ (cm$^{-1}$): 1740, 1660, 1600, 1580 |
| 30 | (3,4-dimethoxyphenyl ring) | —(OCH$_2$CH$_2$)$_3$—H | oil, NMR(CDCl$_3$) δ: 1.13(t, 6H), 3.1–4.2(m, 18H), 3.65 (s, 3H), 3.76(s, 3H), 3.87 (s, 3H), 3.95(s, 3H), 4.43 (t, 2H), 6.6–6.9(m, 4H), 7.59(s, 1H), 12.02(s, 1H) |

TABLE 5-continued (I-d)

Structure: Naphthalene with ring A fused, bearing OH, COR¹, COR², and a phenyl substituent with R³ and R⁴.

| Example Nos. | Compound (I-d) Ring A | R¹ and R² | Physical Properties |
|---|---|---|---|
| 31 | CH₃O-substituted benzene ring (dimethyl) | —(OCH₂CH₂)₃—H | oil, NMR(CDCl₃) δ: 1.15(t, 6H), 1.39(t, 3H), 1.45(t, 3H), 3.87(s, 3H), 3.3–4.4 (m, 22H), 4.43(t, 2H), 6.6–7.7(m, 6H), 12.01 (s, 1H) |

[In Examples 28–30, both of R³ and R⁴ are methoxy group. On the other hand, in Example 31, both of R³ and R⁴ are ethoxy group.]

[Preparation of Starting Compounds]

REFERENCE EXAMPLE 1

(1) 430 ml of 1.55M solution of n-butyl lithium in hexane are added to 800 ml of tetrahydrofuran containing 204.0 g of 2-bromo-3,4,5-trimethoxybenzaldehyde dimethyl acetal. Said addition is carried out at a temperature of −70°~−50° C. for about 15 minutes under stirring. The mixture is stirred at −70°~−60° C. for about 15 minutes, and a solution of 105.5 g of 3,4-dimethoxybenzaldehyde in 300 ml of tetrahydrofuran is added thereto at −70°~−50° C. for about 15 minutes. The mixture is stirred at the same temperature for 15 minutes and poured into 2 liters of water. Further, 4 liters of ethyl acetate are added thereto. After shaking the mixture, the organic layer is separated therefrom, washed with water, dried and filtered to remove inorganic materials. The filtrate is evaporated under reduced pressure to remove the solvent, whereby 266 g of 2-(3,4-dimethoxy-α-hydroxybenzyl)-3,4,5-trimethoxybenzaldehyde dimethylacetal are obtained as yellow oil.

IR$\delta_{Max}^{Nujol}$ (cm⁻¹):3450, 1600

(2) 266 g of the product are dissolved in 95 ml of benzene, and 95 ml of dimethyl acetylenedicarboxylate and 300 mg of p-toluenensulfonic acid monohydrate are added thereto. The mixture is refluxed for 2 hours. The reaction mixture is cooled and evaporated to remove the solvent under reduced pressure. 600 ml of methanol are added to the residue, and the mixture is allowed to stand at −30° C. overnight. Crystalline precipitates are collected by filtration and recrystallized from ethyl acetate, whereby 202 g of 1-(3,4-dimethoxyphenyl)-2,3-bis(methoxycarbonyl)-4-hydroxy-6,7,8-trimethoxynaphthalene are obtained as colorless prisms.

M.p. 178°–179° C.

(3) 100 ml of anhydrous petroleum ether are added to 7.0 g of sodium hydride (61.4% mineral-oil dispersion). After stirring, petroleum ether is removed therefrom. 50 ml of dimethylformamide are added to the residue, and the mixture is cooled at 0° C. A solution of 72.9 g of the product of paragraph (2) in 500 ml of dimethylformamide is added thereto under stirring for 20 minutes. The mixture is stirred at room temperature for one hour. 18 g of methoxymethyl chloride are added thereto at 0° C. for 15 minutes, and the reaction mixture is stirred at room temperature for 2 hours. Then, the reaction mixture is evaporated to remove the solvent under reduced pressure, and the residue is dissolved in 700 ml of ethyl acetate. The solution is washed with water, dried and evaporated to remove the solvent under reduced pressure. The residue is washed with hexane and recrystallied from a mixture of ethyl acetate and hexane, whereby 78 g of 1-(3,4-dimethoxyphenyl)-2,3-bis(methoxycarbonyl)-4-methoxymethoxy-6,7,8-tirmethoxynaphthalene are obtained as colorless needles.

M.p. 93° C.

(4) 14.2 g of the product are dissolved in 420 ml of dioxane. A solution of 16 g of potassium hydroxide in a mixture of 60 ml of water and 120 ml of methanol are added dropwise thereto at 10° C. for 10 minutes. The mixture is allowed to stand at room temperature for 36 hours, and evaporated to remove the solvent under reduced pressure. The residue is dissolved in 800 ml of water. A mixture of 26.8 ml of 35% hydrochloric acid and 100 ml of water is added thereto under stirring and ice-cooling, and the mixture is extracted with chloroform. The extract is washed with water, dried and evaporated under reduced pressure to remove the solvent. The residue is recrystallized from a mixture of ethyl acetate and hexane, whereby 10.5 g of 1-(3,4-dimethoxyphenyl)-2-methoxycarbonyl-4-methoxy-methoxy-6,7,8-trimethoxy-3-naphthoic acid are obtained as colorless prisms.

M.p. 114° C. (decomp.)

REFERENCE EXAMPLES 2 and 3

The corresponding starting compounds are treated in the same manner as described in Reference Example 1, whereby the following compounds are obtained.

(2) 1-(3,4-dimethoxyphenyl)-2-methoxycarbonyl-4-benzyloxy-6,7,8-trimethoxy-3-naphthoic acid.

M.p. 172° C. (decomp.)

(3) 1-(3,4-dimethoxyphenyl)-2-methoxycarbonyl-4-benzyloxy-7,8-methylenedioxy-3-naphthoic acid.

M.p. 222° C.

REFERENCE EXAMPLES 4-7

The corresponding starting compounds are treated in the same manner as described in Reference Example 1-(1), whereby the compounds listed in Table 6 are obtained.

TABLE 6

(III-a) structure: Ring A with Ald substituent, CH(OH) connecting to a phenyl ring bearing $R^3$ and $R^4$.

| Reference Example Nos. | Compound (III-a)[note] Ring A | $R^1$ and $R^2$ | Physical Properties |
|---|---|---|---|
| 4 | dimethylbenzene | —OCH$_3$ | oil |
| 5 | dichloro-dimethylbenzene | —OCH$_3$ | IR$\nu_{Max}^{Nujol}$ (cm$^{-1}$): 3350, 1605, 1600, 1520 |
| 6 | dimethoxy-dimethylbenzene (CH$_3$O, CH$_3$O) | —OCH$_3$ | oil |
| 7 | methoxy-dimethylbenzene (CH$_3$O) | —OC$_2$H$_5$ | oil |

[Ald is —CHO in Example 5, and —CH(OCH$_3$)$_2$ in Examples 4, 6 and 7.]

Note: The products obtained in Reference Examples 4, 6 and 7 are used as the starting compounds of the corresponding Examples without isolation from the reaction solution.

REFERENCE EXAMPLE 8

5.1 g of n-hexyl alcohol and 10.48 g of triphenylphosphine are dissolved in 40 ml of tetrahydrofuran. The solution is cooled at −20° C. A solution of 2.24 g of acetylenedicarboxylic acid and 6.7 g of diazenedicarboxylic acid diethyl ester in 30 ml of tetrahydrofuran is added dropwise thereto under stirring for 15 minutes. Then, the mixture is stirred at room temperature for 2 hours. The reaction mixture is evaporated to remove the solvent under reduced pressure. Hexane is added to the residue, and insoluble materials are removed by filtration. The filtrate is concentrated, and the residue is purified by silica gel chromatography [solvent: hexane-ethyl acetate (4 : 1)], whereby 3.8 g of dihexyl acetylenedicarboxylate are obtained as pale yellow oil.

NMR (CDCl$_3$)δ: 0.8–2.0 (m, 22H), 4.15 (t, 4H)

REFERENCE EXAMPLES 9-14

The corresponding starting compounds are treated in the same manner as described in Reference Example 8, whereby the compounds listed in Table 7 are obtained.

TABLE 7

$R^1$—CO—C≡C—CO—$R^2$ (II)

| Example Nos. | Compound (II) $R^1$ and $R^2$ | Physical properties etc. |
|---|---|---|
| 9 | —OCH(C$_2$H$_5$)$_2$ | oil, NMR(CDCl$_3$) δ: 0.91 (t, 12H), 4.60(q, 4H), 4.70(q, 4H), 4.7–5.0 (m, 2H) |
| 10 | —O—(tetrahydrofuranyl) | oil |
| 11 | —O—CH$_2$—(cyclohexyl) | oil, NMR(CDCl$_3$) δ: 0.7–2.0(m, 22H), 3.95(d, 4H) |
| 12 | —O—CH$_2$—C$_6$H$_5$ | oil, NMR(CDCl$_3$) δ: 5.15 (s, 4H), 7.21(s, 5H) |
| 13 | —(OCH$_2$CH$_2$)$_3$—H | oil, NMR(CDCl$_3$) δ: 1.18 (s, 6H), 3.35–3.9(m, 16H), 4.25–4.50(m, 4H) |
| 14 | —O—n-C$_6$H$_{13}$ | oil, NMR(CDCl$_3$) δ: 0.7–2.0(m, 22H), 4.15(t, 4H) |

What we claim is:

1. A naphthalene derivative of the formula:

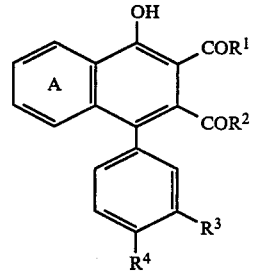

wherein Ring A is an unsubstituted benzene ring, a benzene ring having 1–3 substituent(s) selected from an alkoxy group and a halogen atom, or a benzene ring substituted with a lower alkylenedioxy group; each of $R^1$ and $R^2$ is a group of the formula: —OR$^5$, —NHR$^5$ or

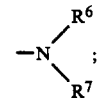

or either one of $R^1$ and $R^2$ is a lower alkoxy group and the other one is a group of the formula: —OR$^5$, —NHR$^5$ or

each of $R^3$ and $R^4$ is a lower alkoxy group, alkoxy group, or one of $R^3$ and $R^4$ is a lower alkoxy group and the other is a hydrogen atom; $R^5$ is selected from the group consisting of
  (i) an alkyl group having at least one substituent selected from the group consisting of a heterocyclic group containing a nitrogen atom, an oxygen atom and/or a sulfur atom, an aryl group, a cycloalkyl group, an alkylthio group, a lower alkoxy group, a lower alkoxycarbonyl group, a lower alkoxy-lower alkoxy group, a mono- or di-lower alkylamino group, an amino group, a thiol group, a hydroxy group, a carboxy group and a halogen atom,
  (ii) a heterocyclic group containing a nitrogen atom, an oxygen atom and/or a sulfur atom,
  (iii) a cycloalkyl group,
  (iv) an alkyl group of at least 5 carbon atoms, and
  (v) an alkenyl group; and each of $R^6$ and $R^7$ is a hydrogen atom or a lower alkyl group, or a salt thereof.

2. The compound according to claim 1, wherein Ring A is an unsubstituted benzene ring, a benzene ring having 1-3 substituent(s) selected from the group consisting of an alkoxy group of 1-4 carbon atoms and a halogen atom, or a benzene ring substituted with an alkylenedioxy group of 1 or 2 carbon atoms; each of $R^1$ and $R^2$ is a group of the formula: $-OR^5$, $-NHR^5$ or

or either one of $R^1$ and $R^2$ is a lower alkoxy group of 1-4 carbon atoms and the other one is a group of the formula: $-OR^5$, $-NHR^5$ or

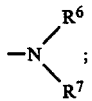

each of $R^3$ and $R^4$ is an alkoxy group of 1-4 carbon atoms, or one of $R^3$ and $R^4$ is an alkoxy group of 1-4 carbon atoms and the other is a hydrogen atom; $R^5$ is selected from the group consisting of
  (i) an alkyl group of 1-4 carbon atoms having 1 or 2 substituent(s) selected from the group consisting of a 5- or 6-membered nitrogen-containing monocyclic heterocyclic group, a phenyl group, a cycloalkyl group of 5-8 carbon atoms, an alkoxy group of 1 or 2 carbon atoms, an alkylthio group of 1 or 2 carbon atoms, an alkoxy-alkoxy group of 2-4 carbon atoms, a dialkylamino group of 2-4 carbon atoms, a hydroxy group and a halogen atom,
  (ii) a 5-or 6-membered nitrogen-containing monocyclic heterocyclic group,
  (iii) a cycloalkyl group of 5-8 carbon atoms,
  (iv) an alkyl group of 5-10 carbon atoms, and
  (v) an alkenyl group of 2-10 carbon atoms; and each of $R^6$ and $R^7$ is hydrogen atom or an alkyl group of 1-4 carbon atoms.

3. The compound according to claim 2, wherein Ring A is an unsubstituted benzene ring, a benzene ring having 1-3 substituent(s) selected from an alkoxy group of 1-4 carbon atoms and a halogen atom or a benzene ring substituted with an alkylenedioxy group of 1 or 2 carbon atoms; each of $R^1$ and $R^2$ is a group of the formula: $-OR^5$, or either one of $R^1$ and $R^2$ is a group of the formula: $-OR^5$ and the other one is an alkoxy group of 1-4 carbon atoms; each of $R^3$ and $R^4$ is an alkoxy group of 1-4 carbon atoms; and $R^5$ is either one of
  (i) an alkyl group of 1-4 carbon atoms having 1 or 2 substituent(s) selected from a 5- or 6-membered nitrogen-containing monocyclic heterocyclic group, phenyl group, a cycloalkyl group of 5-8 carbon atoms, an alkoxy group of 1 or 2 carbon atoms, an alkylthio group of 1 or 2 carbon atoms, an alkoxy-alkoxy group of 2-4 carbon atoms, a dialkylamino group of 2-4 carbon atoms, hydroxy group and chlorine atom,
  (ii) a 5- or 6-membered nitrogen-containing monocyclic heterocyclic group,
  (iii) a cycloalkyl group of 5-8 carbon atoms,
  (iv) an alkyl group of 5-10 carbon atoms or
  (v) an alkenyl group of 2-10 carbon atoms.

4. The compound according to claim 3, wherein Ring A is a benzene ring having three substituents selected from an alkoxy group of 1-4 carbon atoms or a benzene ring substituted with an alkylenedioxy group of 1 or 2 carbon atoms; one of $R^1$ and $R^2$ is a group of the formula: $-OR^5$, and the other is an alkoxy group of 1-4 carbon atoms; each of $R^3$ and $R^4$ is an alkoxy group of 1-4 carbon atoms; and $R^5$ is either one of
  (i) an alkyl group of 1-4 carbon atoms having 1 or 2 substituent(s) selected from a 5- or 6-membered nitrogen-containing monocyclic heterocyclic group, phenyl group, a cycloalkyl group of 5-8 carbon atoms, an alkoxy group of 1 or 2 carbon atoms, an alkylthio group of 1 or 2 carbon atoms, an alkoxy-alkoxy group of 2-4 carbon atoms, a dialkylamino group of 2-4 carbon atoms, hydroxy group and chlorine atom,
  (ii) a 5- or 6-membered nitrogen-containing monocyclic heterocyclic group,
  (iii) a cycloalkyl group of 5-8 carbon atoms,
  (iv) an alkyl group of 5-10 carbon atoms or
  (v) an alkenyl group of 2-10 carbon atoms.

5. The compound according to claim 3, wherein Ring A is an unsubstituted benzene ring or a benzene ring having 1-3 substituent(s) selected from alkoxy groups of 1-4 carbon atoms and halogen atom; each of $R^1$ and $R^2$ is
  (i) an alkoxy group of 1-4 carbon atoms having a substituent selected from phenyl group, a cycloalkyl group of 5-8 carbon atoms and an alkoxyalkoxy group of 2-4 carbon atoms,
  (ii) a cycloalkyloxy group of 5-8 carbon atoms or
  (iii) an alkoxy group of 5-10 carbon atoms; and each of $R^3$ and $R^4$ is an alkoxy group of 1-4 carbon atoms.

6. The compound according to claim 2, wherein Ring A is a benzene ring having three substituents selected from alkoxy groups of 1-4 carbon atoms; either one of $R^1$ and $R^2$ is a phenylalkylamino group of 7 or 8 carbon atoms, a monoalkylamino group of 1-4 carbon atoms or a dialkylamino group of 2-8 carbon atoms, and the other is an alkoxy group of 1-4 carbon atoms; and each of $R^3$ and $R^4$ is an alkoxy group of 1-4 carbon atoms.

7. A pharmaceutical composition, having hypolipidemic activity, which comprises a pharmaceutically acceptable carrier and, as active ingredient, a therapeutically effective amount of a naphthalene derivative or the formula:

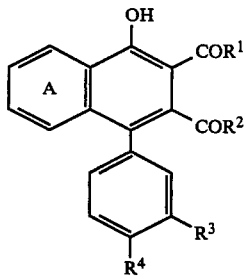

wherein Ring A is an unsubstituted benzene ring, a benzene ring having 1–3 substituent(s) selected from an alkoxy group and a halogen atom, or a benzene ring substituted with a lower alkylenedioxy group; each of $R^1$ and $R^2$ is a group of the formula: —$OR^5$, —$NHR^5$ or

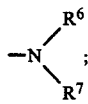

or either one of $R^1$ and $R^2$ is a lower alkoxy group and the other one is a group of the formula: —$OR^5$, —$NHR^5$ or

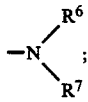

each of $R^3$ and $R^4$ is a lower alkoxy group, alkoxy group, or one of $R^3$ and $R^4$ is a lower alkoxy group and the other is a hydrogen atom; $R^5$ is selected from the group consisting of
  (i) an alkyl group having at least one substituent selected from the group consisting of a heterocyclic group containing a nitrogen atom, an oxygen atom and/or a sulfur atom, an aryl group, a cycloalkyl group, an alkylthio group, a lower alkoxy group, a lower alkoxycarbonyl group, a lower alkoxy-lower alkoxy group, a mono- or di-lower alkylamino group, an amino group, a thiol group, a hydroxy group, a carboxy group and a halogen atom,
  (ii) a heterocyclic group containing a nitrogen atom, an oxygen atom and/or a sulfur atom,
  (iii) a cycloalkyl group,
  (iv) an alkyl group of at least 5 carbon atoms, and
  (v) an alkenyl group; and each of $R^6$ and $R^7$ is a hydrogen atom or a lower alkyl group, or a salt thereof.

8. The composition according to claim 7, wherein Ring A is an unsubstituted benzene ring, a benzene ring having 1–3 substituent(s) selected from the group consisting of an alkoxy group of 1–4 carbon atoms and a halogen atom, or a benzene ring substituted with an alkylenedioxy group of 1 or 2 carbon atoms; each of $R^1$ and $R^2$ is a group of the formula: —$OR^5$, —$NHR^5$ or

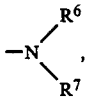

or either one of $R^1$ and $R^2$ is a lower alkoxy group of 1–4 carbon atoms and the other one is a group of the formula: —$OR^5$, —$NHR^5$ or

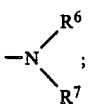

each of $R^3$ and $R^4$ is an alkoxy group of 1–4 carbon atoms, or one of $R^3$ and $R^4$ is an alkoxy group of 1–4 carbon atoms and the other is a hydrogen atom; $R^5$ is selected from the group consisting of
  (i) an alkyl group of 1–4 carbon atoms having 1 or 2 substituent(s) selected from the group consisting of a 5- or 6-membered nitrogen-containing monocyclic heterocyclic group, a phenyl group, a cycloalkyl group of 5–8 carbon atoms, an alkoxy group of 1 or 2 carbon atoms, an alkylthio group of 1 or 2 carbon atoms, an alkoxy-alkoxy group of 2–4 carbon atoms, a dialkylamino group of 2–4 carbon atoms, a hydroxy group and a halogen atom,
  (ii) a 5- or 6-membered nitrogen-containing monocyclic heterocyclic group,
  (iii) a cycloalkyl group of 5–8 carbon atoms,
  (iv) an alkyl group of 5–10 carbon atoms, and
  (v) an alkenyl group of 2–10 carbon atoms; and each of $R^6$ and $R^7$ is hydrogen atom or an alkyl group of 1–4 carbon atoms.

9. The composition according to claim 8, wherein Ring A is an unsubstituted benzene ring, a benzene ring having 1–3 substituent(s) selected from an alkoxy group of 1–4 carbon atoms and a halogen atom or a benzene ring substituted with an alkylenedioxy group of 1 or 2 carbon atoms; each of $R^1$ and $R^2$ is a group of the formula: —$OR^5$, or either one of $R^1$ and $R^2$ is a group of the formula: —$OR^5$ and the other one is an alkoxy group of 1–4 carbon atoms; each of $R^3$ and $R^4$ is an alkoxy group of 1–4 carbon atoms; and $R^5$ is either one of
  (i) an alkyl group of 1–4 carbon atoms having 1 or 2 substituent(s) selected from a 5- or 6-membered nitrogen-containing monocyclic heterocyclic group, phenyl group, a cycloalkyl group of 5–8 carbon atoms, an alkoxy group of 1 or 2 carbon atoms, an alkylthio group of 1 or 2 carbon atoms, an alkoxy-alkoxy group of 2–4 carbon atoms, a dialkylamino group of 2–4 carbon atoms, hydroxy group and chlorine atom,
  (ii) a 5- or 6-membered nitrogen-containing monocyclic heterocyclic group,
  (iii) a cycloalkyl group of 5–8 carbon atoms,
  (iv) an alkyl group of 5–10 carbon atoms or
  (v) an alkenyl group of 2–10 carbon atoms.

10. The composition according to claim 9, wherein Ring A is a benzene ring having three substituents selected from an alkoxy group of 1–4 carbon atoms or a benzene ring substituted with an alkylenedioxy group of 1 or 2 carbon atoms; one of $R^1$ and $R^2$ is a group of the formula: —$OR^5$, and the other is an alkoxy group of 1–4 carbon atoms; each of $R^3$ and $R^4$ is an alkoxy group of 1–4 carbon atoms; and $R^5$ is either one of
  (i) an alkyl group of 1–4 carbon atoms having 1 or 2 substituent(s) selected from a 5- or 6-membered nitrogen-containing monocyclic heterocyclic group, phenyl group, a cycloalkyl group of 5–8 carbon atoms, an alkoxy group of 1 or 2 carbon atoms, an alkylthio group of 1 or 2 carbon atoms, an alkoxy-alkoxy group of 2-4 carbon atoms, a dialkylamino group of 2-4 carbon atoms, hydroxy group and chlorine atom,
(ii) a 5- or 6-membered nitrogen-containing monocyclic heterocyclic group,
(iii) a cycloalkyl group of 5-8 carbon atoms,
(iv) an alkyl group of 5-10 carbon atoms or
(v) an alkenyl group of 2-10 carbon atoms.

11. The composition according to claim 9, wherein Ring A is an unsubstituted benzene ring or a benzene ring having 1-3 substituent(s) selected from alkoxy groups of 1-4 carbon atoms and halogen atom; each of $R^1$ and $R^2$ is
(i) an alkoxy group of 1-4 carbon atoms having a substituent selected from phenyl group, a cycloalkyl group of 5-8 carbon atoms and an alkoxyalkoxy group of 2-4 carbon atoms,
(ii) a cycloalkyloxy group of 5-8 carbon atoms or
(iii) an alkoxy group of 5-10 carbon atoms; and each of $R^3$ and $R^4$ is an alkoxy group of 1-4 carbon atoms.

12. The composition according to claim 8, wherein Ring A is a benzene ring having three substituents selected from alkoxy groups of 1-4 carbon atoms; either one of $R^1$ and $R^2$ is a phenylalkylamino group of 7 or 8 carbon atoms, a monoalkylamino group of 1-4 carbon atoms or a dialkylamino group of 2-8 carbon atoms, and the other is an alkoxy group of 1-4 carbon atoms; and each of $R^3$ and $R^4$ is an alkoxy group of 1-4 carbon atoms.

13. A method for the treatment or prophylaxis of hyperlipidemia, comprising administering to a patient in need of such treatment or prophylaxis a therapeutically effective amount of a compound in accordance with claim 1.

14. A method for the treatment or prophylaxis of hyperlipidemia, comprising administering to a patient in need of such treatment or prophylaxis a therapeutically effective amount of a compound in accordance with claim 2.

15. A method for the treatment or prophylaxis of hyperlipidemia, comprising administering to a patient in need of such treatment or prophylaxis a therapeutically effective amount of a compound in accordance with claim 3.

16. A method for the treatment or prophylaxis of hyperlipidemia, comprising administering to a patient in need of such treatment or prophylaxis a therapeutically effective amount of a compound in accordance with claim 4.

17. A method for the treatment or prophylaxis of hyperlipidemia, comprising administering to a patient in need of such treatment or prophylaxis a therapeutically effective amount of a compound in accordance with claim 5.

18. A method for the treatment or prophylaxis of hyperlipidemia, comprising administering to a patient in need of such treatment or prophylaxis a therapeutically effective amount of a compound in accordance with claim 6.

19. A method for the treatment or prophylaxis of arteriosclerosis, comprising administering to a patient in need of such treatment or prophylaxis a therapeutically effective amount of a compound in accordance with claim 1.

20. A method for the treatment or prophylaxis of arteriosclerosis, comprising administering to a patient in need of such treatment or prophylaxis a therapeutically effective amount of a compound in accordance with claim 2.

21. A method for the treatment or prophylaxis of arteriosclerosis, comprising administering to a patient in need of such treatment or prophylaxis a therapeutically effective amount of a compound in accordance with claim 3.

22. A method for the treatment or prophylaxis of arteriosclerosis, comprising administering to a patient in need of such treatment or prophylaxis a therapeutically effective amount of a compound in accordance with claim 4.

23. A method for the treatment or prophylaxis of arteriosclerosis, comprising administering to a patient in need of such treatment or prophylaxis a therapeutically effective amount of a compound in accordance with claim 5.

24. A method for the treatment or prophylaxis of arteriosclerosis, comprising administering to a patient in need of such treatment or prophylaxis a therapeutically effective amount of a compound in accordance with claim 6.

* * * * *